(12) United States Patent
Rey et al.

(10) Patent No.: US 8,914,102 B1
(45) Date of Patent: Dec. 16, 2014

(54) METHOD AND DEVICE FOR ANESTHESIOLOGY MEASUREMENT AND CONTROL

(75) Inventors: Jose I. Rey, Tampa, FL (US); Richard J. Connolly, Riverview, FL (US); John Anthony Llewellyn, Madeira Beach, FL (US); Mark J. Jaroszeski, Wesley Chaoel, FL (US); Richard Gilbert, Tampa, FL (US)

(73) Assignee: University of South Florida, Tampa, FL (US)

( * ) Notice: Subject to any disclaimer, the term of this patent is extended or adjusted under 35 U.S.C. 154(b) by 1217 days.

(21) Appl. No.: 12/763,740

(22) Filed: Apr. 20, 2010

Related U.S. Application Data

(60) Provisional application No. 61/170,700, filed on Apr. 20, 2009.

(51) Int. Cl.
*A61B 5/05* (2006.01)

(52) U.S. Cl.
USPC ........................................................ 600/547

(58) Field of Classification Search
USPC ........................................................ 600/547
See application file for complete search history.

(56) References Cited

U.S. PATENT DOCUMENTS

| 3,251,361 | A |   | 5/1966 | Rusz |
| 3,598,123 | A |   | 8/1971 | Zaffaroni |
| 4,188,946 | A |   | 2/1980 | Watson et al. |
| 4,533,346 | A | * | 8/1985 | Cosgrove et al. ............... 604/66 |
| 4,570,640 | A |   | 2/1986 | Barsa |
| 5,195,531 | A |   | 3/1993 | Bennett |
| 5,699,808 | A |   | 12/1997 | John |
| 5,775,330 | A |   | 7/1998 | Kangas et al. |
| 5,813,993 | A |   | 9/1998 | Kaplan et al. |
| 5,871,450 | A |   | 2/1999 | Nomura et al. |
| 5,906,208 | A |   | 5/1999 | Ishikawa et al. |
| 6,016,444 | A |   | 1/2000 | John |
| 6,117,075 | A |   | 9/2000 | Barnea |
| 6,274,167 | B1 |   | 8/2001 | Margiotta |
| 6,317,627 | B1 |   | 11/2001 | Ennen et al. |
| 2003/0204329 | A1 | * | 10/2003 | Marchitto et al. ............... 702/31 |
| 2005/0182338 | A1 | * | 8/2005 | Huiku ........................... 600/544 |
| 2007/0010755 | A1 | * | 1/2007 | Sarkela et al. ................. 600/544 |

(Continued)

OTHER PUBLICATIONS

Lackermeier, A. H., et al. "In Vivo ac Impedance Spectroscopy of Human Skin: Theory and Problems in Monitoring of Passive Percutaneous Drug Delivery," Annals of the New York Academy of Sciences. vol. 873. pp. 197-213 (1999).

(Continued)

*Primary Examiner* — Max Hindenburg
*Assistant Examiner* — Renee Danega
(74) *Attorney, Agent, or Firm* — Michele L. Lawson; Smith & Hopen, P.A.

(57) ABSTRACT

Cell or tissue permeability to electrical signals can be used to determine the depth of anesthesia of a patient. A method and device is presented to measure, record and control the effects of anesthesia or analgesics on humans and/or animals. Based on impedance values of tissues measured at single, multiple, or a domain of frequencies, the system detects tissue permeability alterations as determined by electromagnetic, impedance, and/or dielectric spectroscopy. The system measures the permeability of tissues to electrical signals and correlates these values to the depth of anesthesia or sedation level of a certain tissue or individual. This method and device can be used to measure the effects of anesthesia or analgesic for either local or systemic administration.

17 Claims, 13 Drawing Sheets

(56) References Cited

U.S. PATENT DOCUMENTS

2007/0132043 A1    6/2007  Bradley et al.
2008/0021339 A1*   1/2008  Gabriel et al. ............... 600/532
2009/0005655 A1    1/2009  Frank et al.
2010/0081903 A1*   4/2010  Izzetoglu ..................... 600/328

OTHER PUBLICATIONS

Woolfson, D. et al. "A.C. Impedance Spectroscopy of Percutaneous Local Anaesthetics," European Journal of Pharmaceutical Sciences,. vol. 4. pp. S145-S145 (1996).

Sawaguchi, Y. et al. "A Model-Predictive Hypnosis Control System Under Total Intravenous Anesthesia," IEEE Transactions on Biomedical Engineering. vol. 55. No. 3. pp. 874-887 (2008).

Yardimci, A. et al. "Microcontroller Based Fuzzy Logic Sevofluorane Anesthesia Control System," B. Reusch (Ed.): Fuzzy Days 2001, LNCS 2206. pp. 137-147 (2001).

Heimburg T. et al. "The Thermodynamics of General Anesthesia," Biophysical Journal. vol. 92. pp. 3159-3165 (2007).

Blicher, K. et al. "The temperature dependence of lipid membrane permeability, its quantized nature, and the influence of anesthetics," Arxiv preprint arXiv:0807.4825. pp. 1-12 (2008).

Ivorra, A. et al. "In vivo electrical impedance measurements during and after electroporation of rat liver," Bioelectrochemistry. vol. 70. pp. 287-295 (2007).

Absalom, N. et al. Closed-loop Control of Anesthesia Using Bispectral Index. Anesthesiology—Performance Assessment in Patients Undergoing Major Orthopedic Surgery Under Combined General and Regional Anesthesia. vol. 96. pp. 67-73 (2002).

Gupta et al., Inhaled Anesthesia: The Original Closed-Loop Drug Administration Paradigm, Clinical Pharmacology & Therapeutics, 2008, vol. 84, No. 1, pp. 15-18.

Sawaguchi et al., An Intravenous Anesthesia Control System with Pharmacodynamics Identification Function, Shisutemu, Joho Bumon Gakujutsu Koenkai Koen Ronbunshu, 2001, vol. 2001, pp. 319-324.(Abstract Only).

* cited by examiner

METHOD AND DEVICE FOR ANESTHESIOLOGY MEASUREMENT AND CONTROL

CROSS REFERENCE TO RELATED APPLICATION

This application claims priority to U.S. Provisional Patent Application No. 61/170,700, entitled "Anesthesiology Measurement and Control System", filed on Apr. 20, 2009, the contents of which are herein incorporated by reference.

FIELD OF INVENTION

This invention relates to anesthesiology, more specifically monitoring and controlling the level of sedation or depth of anesthesia in a patient.

BACKGROUND OF THE INVENTION

Anesthesiology involves the delivery of anesthetic agents to a patient prior to and/or during a procedure; if the proper dose of anesthesia is delivered, the patient will be relieved from pain and sensory burden of the procedure with minimal side effects.

The depth of anesthesia has been historically measured subjectively by the anesthesiologist through observing various physiological variables including changes in systolic and diastolic blood pressure, heart rate or respiration rate of the patient or by observing a reflex of the eyelashes, a dimension of the pupil, a hue of a limb or the body temperature of the patient.

Anesthesia can be applied locally (delivered by transdermal, transmucosal, topical, or parental means) or delivered as a general anesthetic (delivered by inhalation, or parenteral or rectal means). Local anesthesia delivers loss of sensation to a specific region of the body while consciousness is maintained while general anesthesia causes a progressive depression of the central nervous system and a reversible loss of consciousness.

Local anesthetics are membrane stabilizing drugs which reversibly decrease the rate of depolarization and repolarization of excitable membranes. Local anesthetic drugs act mainly by inhibiting sodium influx through sodium-specific ion channels in the neuronal cell membrane, such as the voltage-gated sodium channels. When the influx of sodium is interrupted, an action potential cannot arise and signal conduction is inhibited. The receptor site is thought to be located at the cytoplasmic portion of the sodium channel. Local anesthetic drugs bind more readily to sodium channels in the activated state which is referred to as a state-dependent blockade, thus onset of neuronal blockade is faster in neurons that are rapidly firing.

Local anesthetics are weak bases and are usually formulated as the hydrochloride salt to render them water-soluble. At the chemical's pKa the protonated (ionized) and unprotonated (unionized) forms of the molecule exist in equilibrium but only the unprotonated molecule diffuses readily across cell membranes. Once inside the cell the local anesthetic will be in equilibrium, with the formation of the protonated (ionized form), which does not readily pass back out of the cell. In the protonated form, the molecule binds to the local anesthetic binding site on the inside of the ion channel near the cytoplasmic end.

All nerve fibers are sensitive to local anesthetics, but generally, those with a smaller diameter tend to be more sensitive than larger fibers. Local anesthetics block conduction in the following order: small myelinated axons (e.g. those carrying nociceptive impulses), non-myelinated axons, and finally large myelinated axons.

Local anesthesia can be delivered in many forms including topically (surface anesthesia), infiltration, plexus block, epidural (extradural) block and spinal anesthesia (subarachnoid block). Local anesthesia administered topically can be applied through the use of an anesthetic patch. Anesthetic patches are well known in the art and typically consist of an adhesive patch that is suitable for carrying any type of topical anesthetic.

The objectives of general anesthesia include blocking the patient's movements, relieving the patient's pain (analgesia), causing the patient to lose consciousness and be unaware of the operation and keep blood pressure above a given threshold (generally blood pressure should not be below 50 mm Hg for mean arterial pressure). General anesthesia generally produces an irregular descending paralysis of the central nervous system and suppression of the sensory cortex.

In general anesthesia the anesthesiologist administers one or more volatile liquids or gases such as nitrous oxide, isoflurane, desflurane, ethylene, cyclopropane, ether, chloroform, halothane, sevoflurane etc. Non-volatile drugs, such as pentothal, propofol, sodium thiopental, ketamine, etomydate, evipal and procaine, can alternatively be administered by injection or intravenous (IV) infusion. Onset of anesthesia is faster with intravenous administration than with inhalation taking about 10-20 seconds to induce total unconsciousness. However, inhalation is preferred in cases where IV access is difficult to obtain, where difficulty maintaining the airway is anticipated, or where the patient prefers inhalation. In order to prolong anesthesia for the duration of the surgery, the level of anesthesia used to induce the anesthetic effect must be maintained. In the case of general anesthesia administered through inhalation, the patient normally breathes in a carefully controlled combination of oxygen, nitrous oxide and a volatile anesthetic agent. Inhaled general anesthetics can be supplemented during the operation with IV anesthetics such as opiods or sedative-hypnotics.

Generally with respect to administering anesthesia through inhalation, a modern machine typically includes the following components: (1) pipeline connections to piped hospital oxygen, medical air, and nitrous oxide; (2) reserves in gas cylinders of oxygen, air, and nitrous oxide attached via a specific yoke with a Bodok seal. Older machines may have cylinder yokes and flow meters for carbon dioxide and cyclopropane; (3) a high-flow oxygen flush which provides pure oxygen at 30 liters/minute; (4) pressure gauges, regulators and 'pop-off' valves, to protect the machine components and patient from high-pressure gases (referred to as 'barotrauma'); (5) flow meters (rotameters) for oxygen, air, and nitrous oxide, which are used by the anesthesiologist to provide accurate mixtures of medical gases to the patient. Flow meters are typically pneumatic, but increasingly electromagnetic digital flow meters are being used; (6) one or more anesthetic vaporizers to accurately add volatile anesthetics to the fresh gas flow; (7) a ventilator; (8) physiological monitors to monitor the patient's heart rate, ECG, non-invasive blood pressure and oxygen saturation; (9) breathing circuits, most commonly a circle attachment, or a Bain's breathing system, which are breathing hoses connected to an anesthesia face mask; (10) a heat and moisture exchanger (HME) with or without bacteria-viral filter (HMEF); (11) a scavenging system to remove expired anesthetic gases from the operating room; and (12) a suction apparatus.

Complications in anesthesia are commonly the result of an improper dose administration. For example, if a supra-optimal amount of anesthesia is delivered to the point of toxicity, morbidity or mortality can ensue whereas if a suboptimal amount of anesthesia is delivered, the patient might wake, sense pain, or develop anesthesia awareness. Neurological monitors measure neurological function but will not work properly under many general anesthesia cases nor be adequate for local anesthesia. In 2007, anesthesia complications reached 215,000 worldwide (resulting in 1,500+ deaths), 40,000 in the United States (resulting in 265 deaths), and 46,000 in Europe (resulting in 320 deaths).

The proper dose of anesthesia or analgesia is dependent on many variables that include dosage, temperature and pressure. (T. Heimburg and A. D. Jackson, "The Thermodynamics of General Anesthesia," *Biophysical Journal*, vol. 92, p. 3159 (2007)). The effect of anesthesia is related to lipid membrane permeation to ions and molecules; in addition, this "permeation" may be due in part to protein channels. (A. Blicher, K. Wodzinska, M. Fidorra, M. Winterhalter, and T. Heimburg, "The temperature dependence of lipid membrane permeability, its quantized nature, and the influence of anesthetics," Arxiv preprint arXiv:0807.4825 (2008)). Cell membrane permeability to ions and other molecules can be measured as a parameter of electromagnetic or dielectric parameters on a single, multiple or domain of frequencies. (A. Ivorra and B. Rubinsky, "In vivo electrical impedance measurements during and after electroporation of rat liver," *Bioelectrochemistry*, Vol. 70, pp. 287-295 (2007)). Impedance spectroscopy can be used to measure electromagnetic or dielectric parameters by using a range of AC frequencies. Living tissue is composed of cells, which are surrounded by a lipid membrane. Between the cells, there is extracellular material that may contain extracellular fluids of varied conductivity. Electrical DC and low frequency currents are limited to the extra cellular space. With increasing AC frequency the impedance of the cell membrane decreases. The inventors have developed a method and device to measure the depth of sedation in a patient who was administered either local or general anesthesia by measuring cell permeability in tissues through impedance spectroscopy.

DESCRIPTION OF THE PRIOR ART

Related Art in Inhaled Anesthesia Devices:

Several patents describe monitoring various physiological characteristics of a patient under anesthesia, however none of the patents measure dielectric impedance directly from tissues as a function of cell permeability to determine sedation level or depth of anesthesia as does the present patent. Several patents have measured gas exhaled by a subject including U.S. Pat. No. 4,188,946 which describes a feedback loop to control the dose of anesthetic using a CO2 analyzer that uses impedance measurements on the gas exhaled by the subject and U.S. Patent Application 2007/0132043 A1 and U.S. Patent Application U.S. 2008/0021339 A1 which describe impedance spectroscopy measurements on gases as a breath analysis tool. In addition, monitoring brain activity patterns (U.S. Pat. No. 6,016,444); monitoring microexpressions of the face (U.S. Pat. No. 5,195,531); measuring skin temperature (U.S. Pat. No. 6,117,075); and measuring the ratio of two signals from an electrocardiographic waveform detecting device which measures pulse periods (U.S. Pat. No. 5,871,450). None of the above-mentioned art monitors electromagnetic or dielectric impedance for sedation level as a function of cell permeability as is claimed in the instant invention.

Related Art in Anesthesia Patch and Local Anesthesia Measurement:

Similarly to the related art for inhaled anesthesia devices, none of the art related to patch or local anesthesia measurement discloses monitoring electromagnetic or dielectric impedance for sedation level as a function of cell permeability. The art in this area includes patents generally describing the use of an adhesive patch for drug delivery including local anesthesia (U.S. Pat. Nos. 3,598,123 and 6,274,167). Also disclosed in this area is an apparatus and method to deduce the depth and level of anesthetic agents for spinal and epidural nerve blocks in which nerves are stimulated with an electrical signal and physiological responses are monitored (U.S. Pat. No. 4,570,640). In contrast to the above-referenced patents, the present invention examines direct electrical characteristics (impedance information) as opposed to physiological responses.

Related Art in Measurements of Electrical Properties During Anesthesia Application:

Lackermeier et al. measured impedance during anesthesia administration of an anesthetic, but only looked for the direct changes of the amount of drug delivered and the diffusion of drug through the stratum corneum. They attributed the effect to the concentration of the drug, and not the membrane permeability, or sedation level. The present invention differs by using impedance data directly from tissues as a function of cell permeability to determine the sedation level or depth of anesthesia. (A. H. Lackermeier, E. T. McAdams, G. P. Moss, and A. D. Woolfson, "In Vivo ac Impedance Spectroscopy of Human Skin: Theory and Problems in Monitoring of Passive Percutaneous Drug Delivery," *Annals of the New York Academy of Sciences*, vol. 873, pp. 197-213, (1999); A. D. Woolfson, D. McCafferty, G. Moss, E. MacAdams, and A. Lackermier, "A.C. impedance spectroscopy of percutaneous local anaesthetics," *European Journal of Pharmaceutical Sciences*, vol. 4, pp. S145-S145 (1996)).

U.S. Pat. No. 5,906,208 describes a method and apparatus to determine the depth of anesthesia based on the changes of electrical potentials in the skin, relative to data collected prior to anesthetic exposure. However, this patent does not measure impedance data directly from tissues as a result of cell membrane permeability.

As shown above, none of the known prior art measures impedance data obtained directly from tissues as a result of cell membrane permeability to determine the depth of anesthesia (sedation level).

SUMMARY OF INVENTION

In one embodiment of the present invention is a method of measuring the depth of anesthesia in a patient comprising providing at least one electrode to interrogate at least one electromagnetic property of at least one cell of the patient. A control unit is also provided which receives data from the electrode to measure at least one electromagnetic property. The data is then correlated to the level of sedation using an algorithm and observed events in the patient such as rate of respiration. The electrodes can be contact electrodes, non-contact electrodes, surface electrodes, penetrating electrodes, or implantable electrodes. The electromagnetic properties measured can be resistance, reactance, impedance, mechanical permeability, electrical permeability, capacitance, phase angle or zeta potential. The electromagnetic property is measured at least one frequency but can be measured at multiple or a domain of frequencies.

In another embodiment is a method of measuring the depth of anesthesia in a patient by providing at least one electrode to interrogate the permeability of at least one cell of a patient; providing a control unit to receive data from the electrode and measure the permeability of the cell to an electrical signal; and correlating the measurement data to the level of sedation through the use of an algorithm and observable events in the patient such as rate of respiration. The permeability of the cell is measured at least one frequency.

Another embodiment describes a method of measuring and controlling the depth of anesthesia by providing an electromagnetic wave propagation system to interrogate at least one electromagnetic property of at least one cell of the patient; providing a control unit to measure the electromagnetic property of the cell; and correlating the measurement data to the level of sedation. The electromagnetic wave propagation system can be a system that uses ion deposition waves, ultrasound waves or microwaves. The electromagnetic properties measured can be resistance, reactance, impedance, mechanical permeability, electrical permeability, capacitance, phase angle or zeta potential. The electromagnetic properties can be measured at one frequency or at a multiple or domain of frequencies.

In another embodiment of the present invention is a device for measuring and controlling the depth of anesthesia that is comprised of at least one electrode and a control unit containing a microprocessor which receives data from the electrode. In the case of general anesthesia, a vaporizer is connected to the control unit to dispense anesthesia. The electrodes can be contact electrodes, non-contact electrodes, surface electrodes, penetrating electrodes, or implantable electrodes.

Also provided herein is a device for measuring and controlling the depth of anesthesia that is comprised of an adhesive patch having an anesthesia reservoir, at least one electrode and a control unit containing a microprocessor to receive data from the electrode. Additionally, the anesthesia reservoir can contain microvalves which deliver the anesthesia to the skin.

In another embodiment, a device for measuring and controlling the depth of anesthesia is provided which is comprised of a syringe having a needle end and a base end. The needle contains at least one electrode. The base is connected to the needle on one end and contains a control unit having a microprocessor which receives data from the electrode to measure the electromagnetic properties of the cell or tissue of the patient.

BRIEF DESCRIPTION OF THE DRAWINGS

For a fuller understanding of the invention, reference should be made to the following detailed description, taken in connection with the accompanying drawings, in which.

Isoflurane level is dropped to 0% at reading 20 leading to the subject returning to consciousness in step 24.

Figure 13:
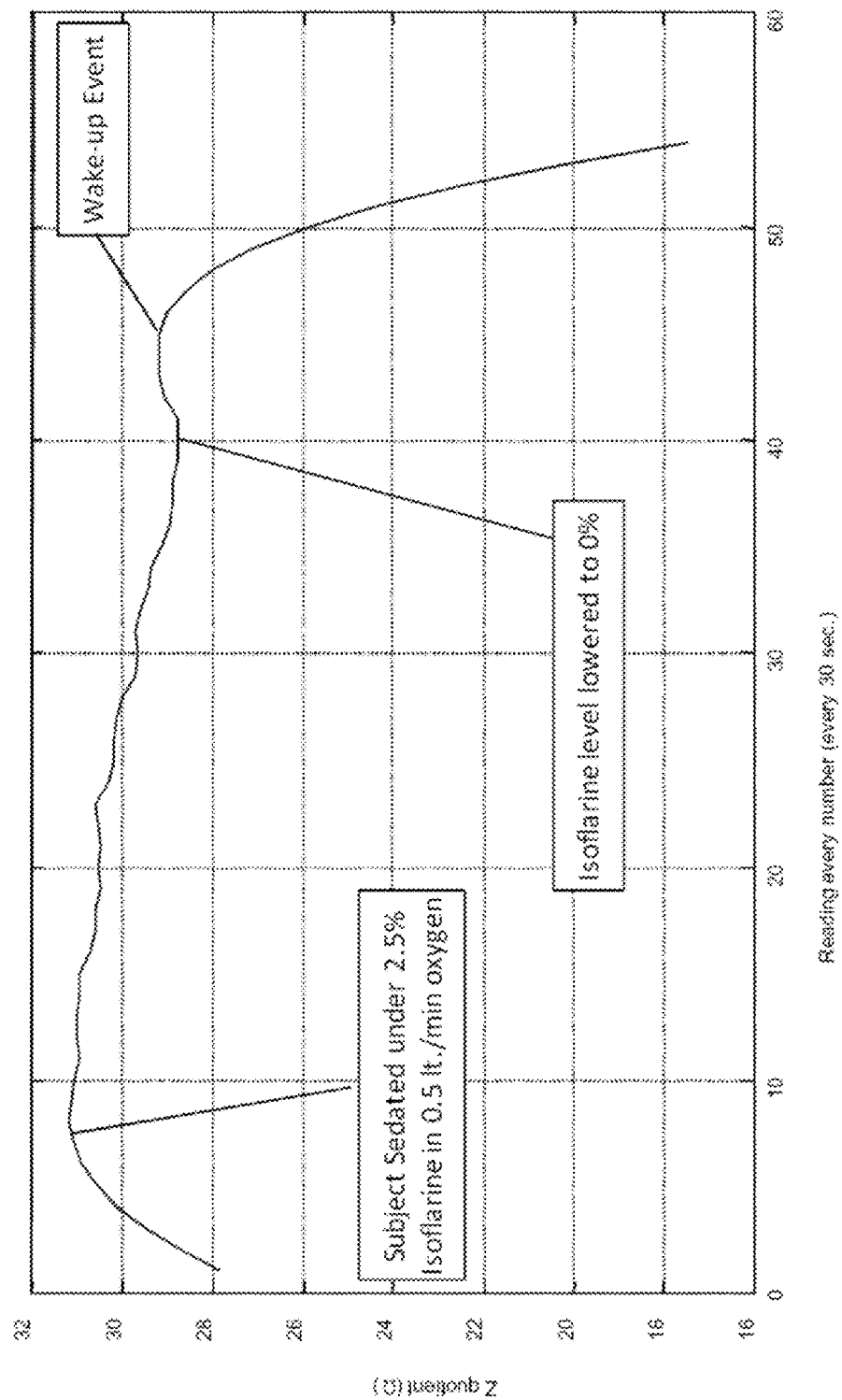

FIG. 13 is a graph depicting an impedance quotient calculated from two different frequencies which shows readings from an animal model's tissue after the subject has been sedated. During the first 40 readings the dose of isoflurane (2.5% isoflurane in 0.5 lt/min oxygen flow) is kept constant. Isoflurane level is dropped to 0% at reading 40 leading to the subject returning to consciousness in step 46.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

"Patient" as used herein describes any animal or human to which an anesthetic has been administered. The anesthetic can be administered by any means well known to those in the art and includes local and general anesthesia.

"Depth of anesthesia", "sedation level" and "level of consciousness" are used interchangeably herein to refer to the level of patient awareness and analgesia related to the amount of anesthesia administered to the patient.

"To interrogate" as used herein refers to the use of at least one electrode or electromagnetic wave propagation system to send an electrical signal to at least one cell and receive data back from the at least one cell to determine the changes in the electromagnetic properties of the cell. These changes are used to correlate the changes in electromagnetic properties of the cell to the level of sedation or depth of anesthesia. Both contact (electrodes physically in contact with the cell or tissue) and non-contact (where one or a set of antennae are directed to the tissue or cell to transmit an electrical signal) electrodes can be used to interrogate the cell and gather measurement data. The electromagnetic wave propagation system can include, but is not limited to, ion deposition, ultrasound waves and microwaves. The changes in electromagnetic properties can include, but are not limited to, cell permeability or impedance.

The present invention provides a method and apparatus used to measure, analyze, and control the level of sedation in local, regional, or general tissues influenced by anesthesia. The invention monitors the depth of anesthesia, the sedation level of the patient and the level of consciousness of the patient while under anesthesia.

The invention functions by measuring the electromagnetic, chemical or mechanical properties of a cell, group of cells, tissue or bodily fluid on at least one frequency. Alternatively, multiple or a domain of frequencies can be measured. The properties that can be measured by the instant invention include, but are not limited to, resistance, reactance, impedance, mechanical permeability, electrical permeability, permittivity, capacitance, phase angle, and zeta potential.

The invention can be used on an animal or human, and any tissue that may be affected by anesthesia, including but not limited to, the skin, muscle, nervous system (both central and peripheral), blood, liver, kidney, intestines, mucosal tissue, or buccal or gum tissue (for dental use). Anesthesia changes the characteristics of the cell membrane of nervous cells. The degree to which anesthesia affects a patient depends on the lipid composition of the membrane. Since anesthesia affects all membranes in all cells that are exposed to it, the same phenomena of cell permeability can be measured in all affected cells, not just neuronal cells. For general anesthesia, most of the cells in the body are affected while in local anesthesia most of the cells in the localized area are affected. Since all cells have membranes and all tissues have cells, the effect of anesthesia can be measured indirectly by measuring the effect on the cells of a tissue without having to measure the nervous cells affected. Measuring the electrical characteristics of a cell allows the degree of change at the tissue, cell and cell membrane level to be assessed.

Several different types of electrodes can be used in conjunction with the present invention. The tissues, cells or bodily fluids can be probed using contact or non-contact electrodes to measure and control level of sedation. Non-contact electrodes can be one or a set of antennae that are directed to the skin in a certain area of the patient under anesthesia. Ionized gas can be used as an electrode. The electrodes can be a single or a set of contact or non-contact electrodes probing any tissue, for example the skin on a limb of the subject under anesthesia. Surface electrodes (those that are positioned superficially on the surface of the skin of a patient) can be used as well as penetrating electrodes (those that can pierce through the skin of a patient) or any system that employs electrodes that are in contact with a tissue. The electrodes can be implanted, superficial, or part of an invasive or non-invasive instrument or drug delivery system. Implanted electrodes can be any electrode contained within the patient and do not necessarily have to be in contact with the interrogating equipment. An invasive instrument is an implanted instrument containing electrodes which is implanted within a patient's body. A non-invasive instrument refers to an instrument containing electrodes that is positioned external to the patient's body. The electrodes can also be part of a drug delivery system such as a catheter, a needle or a drug delivery patch.

The electrodes transmit an electromagnetic signal at a single, multiple or domain of frequencies that can be transmitted through or reflected by a single type or multiple tissues to and from the electrodes. Signals that are transmitted through a patient's tissue are those signals that go from one electrode to another through the tissue. Signals that are reflected by an electrode refers to those signals in which the same electrode is transmitting a signal into a patient and receiving a bounced back signal from the patient that can be used to determine impedance. The electrodes and system can be contained within a single chip device or packaged as a small-scale circuit.

Alternatively, non-contact methods can be utilized to measure frequencies including but not limited to, ion deposition, ultrasound waves, microwaves, or other methods that use an electromagnetic wave propagation system. The data can be generated by magnetic acoustic methods such as using electromagnetic acoustic resonance in the form of submitting a tissue to ultrasound waves in a magnetic field to generate impedance signals.

The tissue response to the electric signal is then processed and the resulting data and derivatives are analyzed to yield dielectric, or electromagnetic characteristics of the tissue that reflect the level of sedation of the tissue, a peripheral tissue, or the subject in general. The dielectric or electromagnetic measured characteristics are processed to assess level and change in permeation of the cells in the tissues as affected by anesthesia or analgesia agents. The control unit can determine the level of anesthesia to deliver using information from the impedance measurements. An upper or lower threshold limit or an algorithm to determine the level can be hard-wired into computer hardware, for example in a chip, CPU, EPROM, etc. or alternatively the threshold limits or algorithm can be part of computer software. The threshold limits can be one limit or a set of threshold limits including upper and lower limits. The algorithm is any algorithm that can be used to calculate how much anesthesia to deliver, such as a fuzzy logic algorithm or an expert system. The system may also determine other variables such as temperature, pressure, etc.

The invention can be used as a stand-alone device, or in conjunction with other sedation and subject health measurement devices such as electroencephalogram equipment, thermometers, pulse oximeters, capnographs, and/or peak flowmeters.

Figure 1:
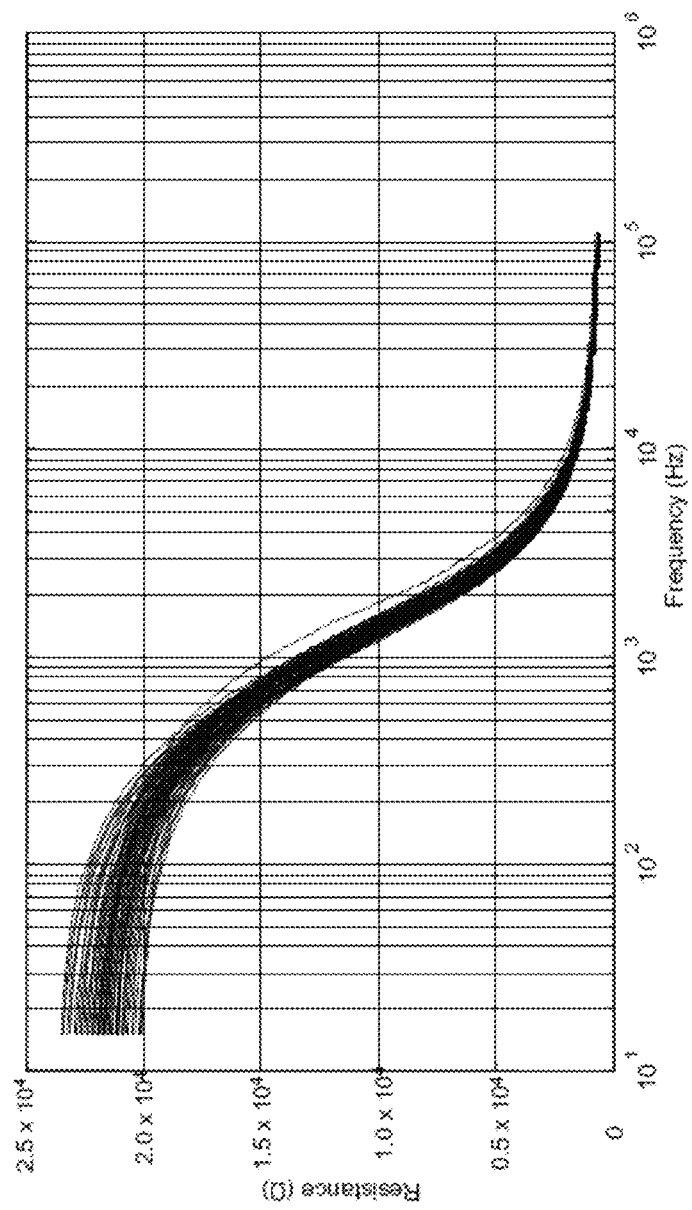
FIG. 1 is a graph depicting several measured tissue resistance (R–in Ohms) or real part of the impedance values across multiple frequencies. Each curve in the graph represents a multi-frequency reading along different frequency values.
Figure 2:
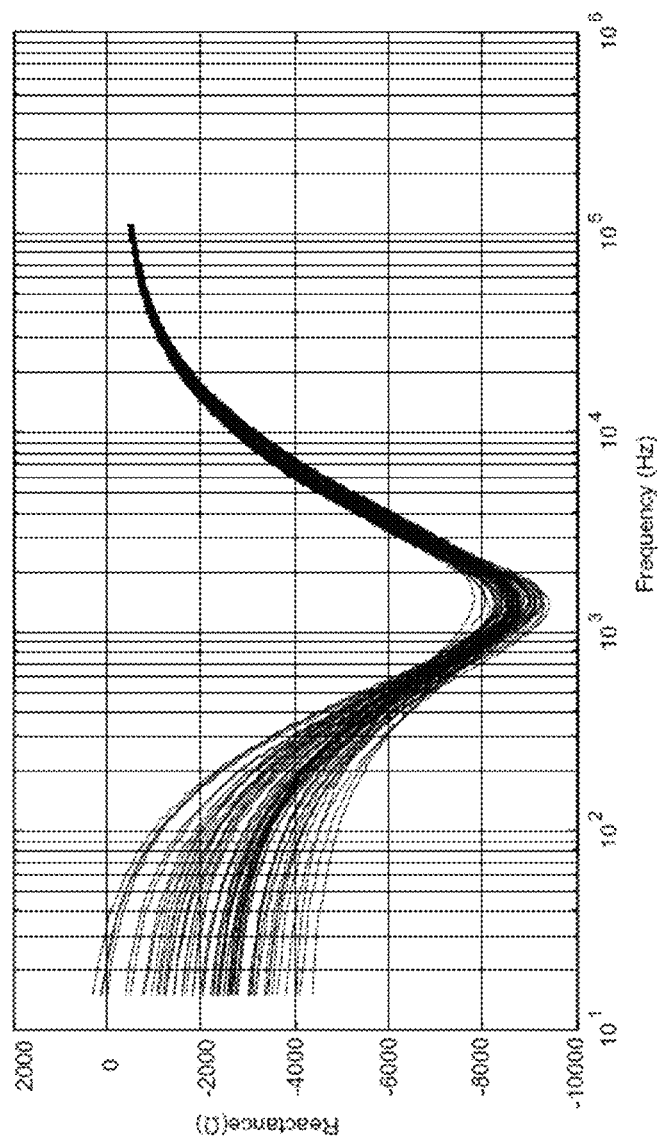
FIG. 2 is a graph depicting several measured tissue reactance (X–in Ohms) or imaginary part of the impedance values across multiple frequencies. Each curve in the graph represents a multi-frequency reading along different frequency values.
Figure 3:
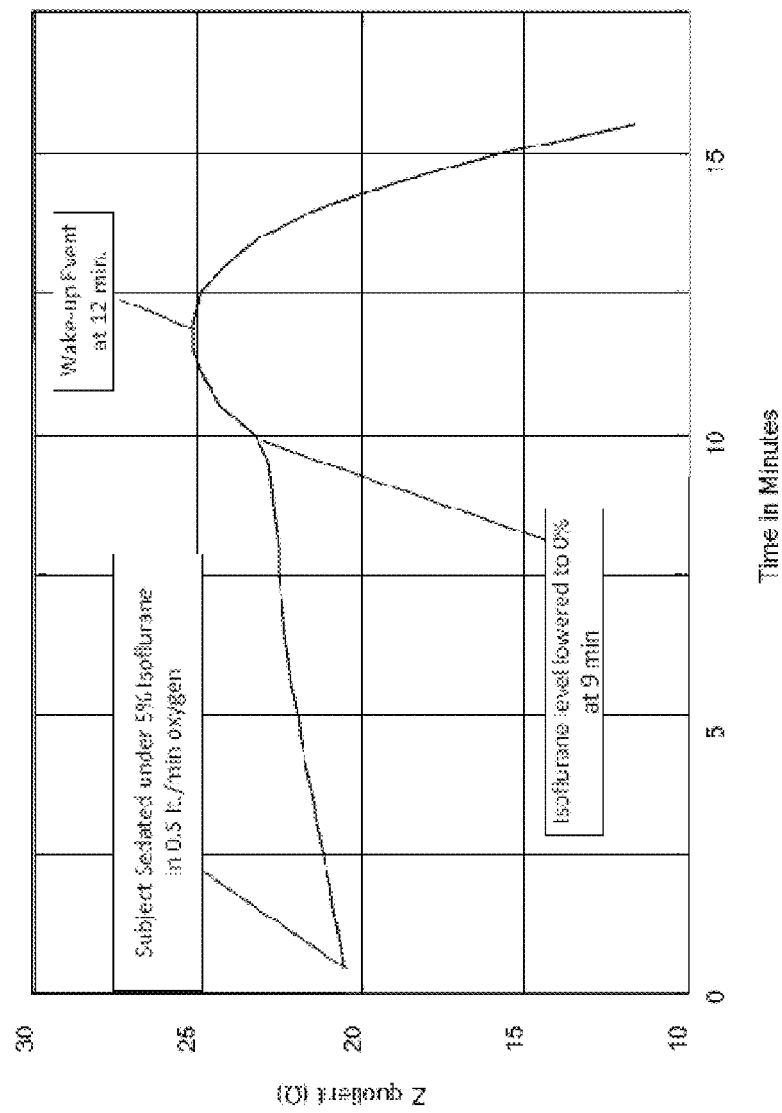
FIG. 3 is a graph depicting an impedance quotient calculated by dividing resistance at two different frequencies (1 KHz and 10 KHz in this case) which shows readings from an animal model's tissue after the subject has been sedated. During the first 9 minutes the dose of isoflurane (5% isoflurane in 0.5 lt/min oxygen flow) is kept constant. Isoflurane level is dropped to 0% at 9 minutes leading to the subject returning to consciousness at 12 min.
Figure 4:
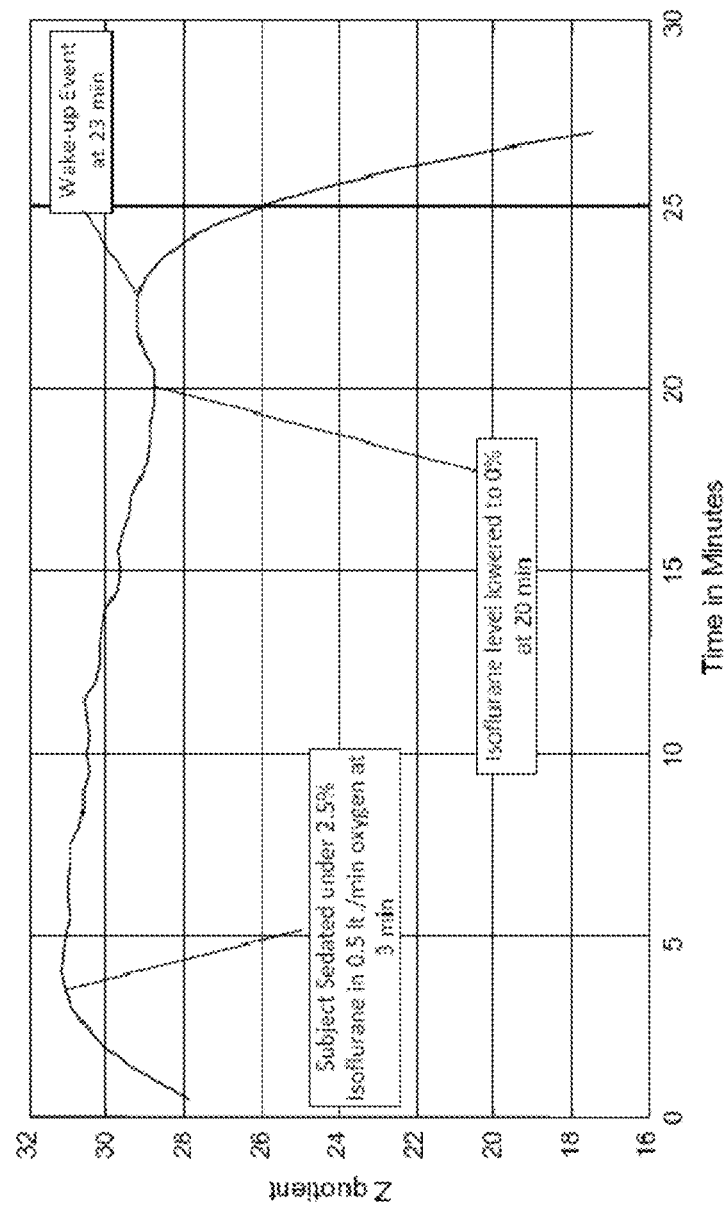
FIG. 4 is a graph depicting an impedance quotient calculated by dividing resistance at two different frequencies which shows readings from an animal model's tissue after the subject has been sedated. During the first 20 minutes the dose of isoflurane (2.5% isoflurane in 0.5 lt/min oxygen flow) is kept constant. The level of isoflurane is dropped to 0% at reading 20 minutes to the subject returning to consciousness at 23 minutes.

FIG. 1 illustrates the measured tissue resistance values across multiple frequencies. FIG. 2 illustrates measured tissue reactance of impedance values across multiple frequencies. FIGS. 3 and 4 are graphs depicting impedance quotients calculated by dividing resistance quotients at two different frequencies.

General Anesthesia Measurement and Control

Figure 5:
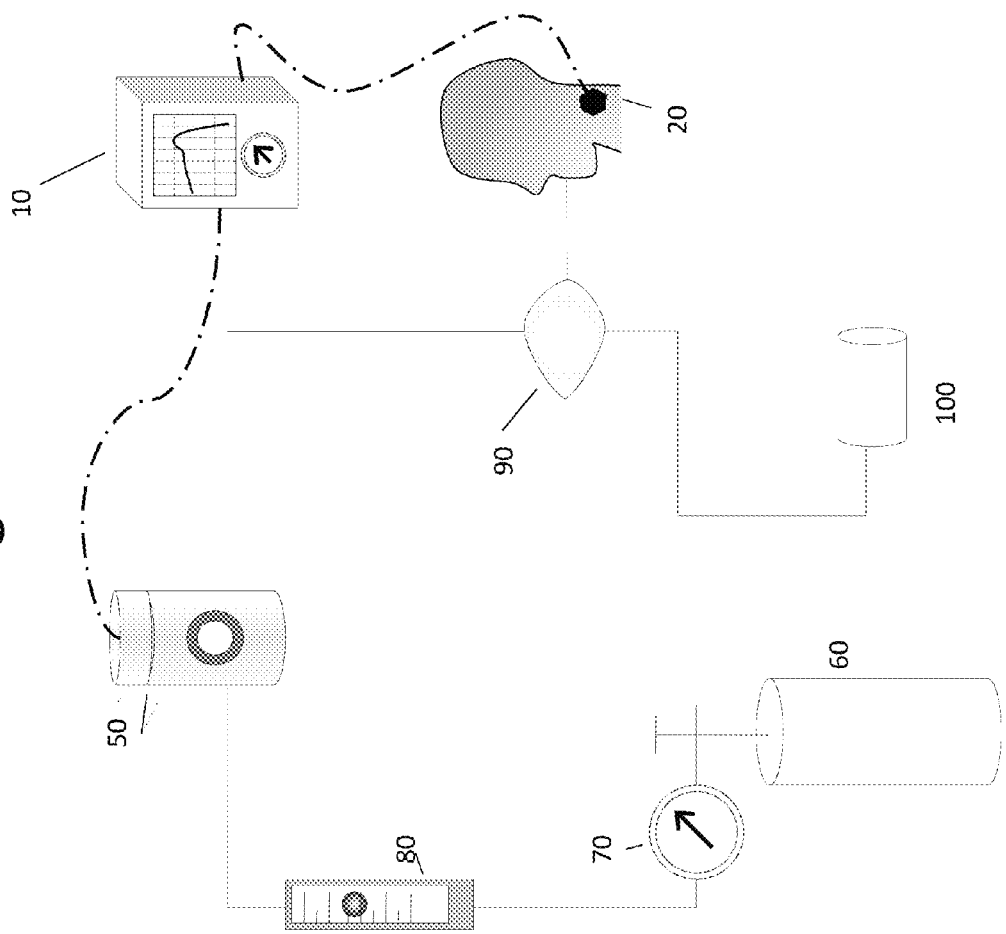
FIG. 5 is an image of a general anesthesia inhalation system in which the dose is regulated by the flow of oxygen and the amount of anesthesia vaporized into the breathing gas mix. The system is generally comprised of an oxygen or breathing gas supply, a flow regulator, a Rotometer, a vaporizer, an anesthesia bag, and a scavenge system. The dashed lines show the addition of the control system of the present invention to measure the patient's electromagnetic or dielectric impedance and regulate the flow of oxygen and amount of anesthesia delivered. As shown in the figure, in one embodiment of the present invention, at least one electrode can be attached to a patient (for example on the neck of the patient). This electrode then connects to the control unit which measures the impedance data. The control unit is also connected to the vaporizer of the system and can regulate the amount of anesthesia delivered to the patient in accordance with the impedance measurement.

In this embodiment, the invention includes a device with an indicator for level of sedation based on readings in any tissue of the subject under anesthesia, thus permitting the anesthesiologist to modify dosage or any of the other variables involved in delivering the anesthesia. The invention can be used in a close loop anesthesia controller to automatically adjust the variables responsible for the sedation of the subject under general anesthesia. A general anesthesia inhalation system integrating the anesthesia measurement and control device is shown in FIG. 5. A general anesthesia inhalation system is generally comprised of an oxygen supply tank (60) which is connected to a regulator (70) to provide a workable low-pressure gas stream from the oxygen supply tank (60). A rotameter (80) is a component of the system and measures the flow rate of gas in a closed tube. A vaporizer (50) is used to dispense the anesthetic agent to the patient. The oxygen and anesthesia are administered to the patient through a reservoir bag (90) that covers the patient's mouth and nose to ensure that the gases are inhaled. A scavenge system (100) is connected to the reservoir bag (90) to collect the exhaled gases from the patient.

As shown in FIG. 5, the control unit (10) can be connected to the patient by an electrode (20) placed on the patient's skin. The electrode (20) transmits electrical signals directly to a tissue or cell and the permeability or impedance of the tissue or cell to the electrical signal is sent back through the electrode (20) to the control unit (10) where the data can be analyzed. A wire (30) then leads from the electrode (20) to the control unit (10). A second wire (40) leads from the control unit (10) to a vaporizer (50) dispensing anesthesia. The control unit (10) monitors the level of sedation (depth of anesthesia) of the patient through the electrode (20) placed on the patient's skin. Impedance measurements of electrophysiological activity due to cell membrane permeability or impedance are transmitted through the electrode (20) to the control unit (10). The control unit (10) can then adjust the anesthesia released from the vaporizer.

Local Anesthesia Delivered Topically Through the Skin

In this embodiment, the invention can be used as a separate measurement device to assess the sedation of the local area on the subject. In this embodiment, the electrodes (10) are applied to the patient's skin. For topical delivery through the skin, the invention can be a self-contained delivery patch (110) in which the amount of anesthesia or analgesic delivered is controlled in a closed loop by analyzing the electromagnetic or dielectric readings from the subject's affected area or a nearby area.

Figure 6:
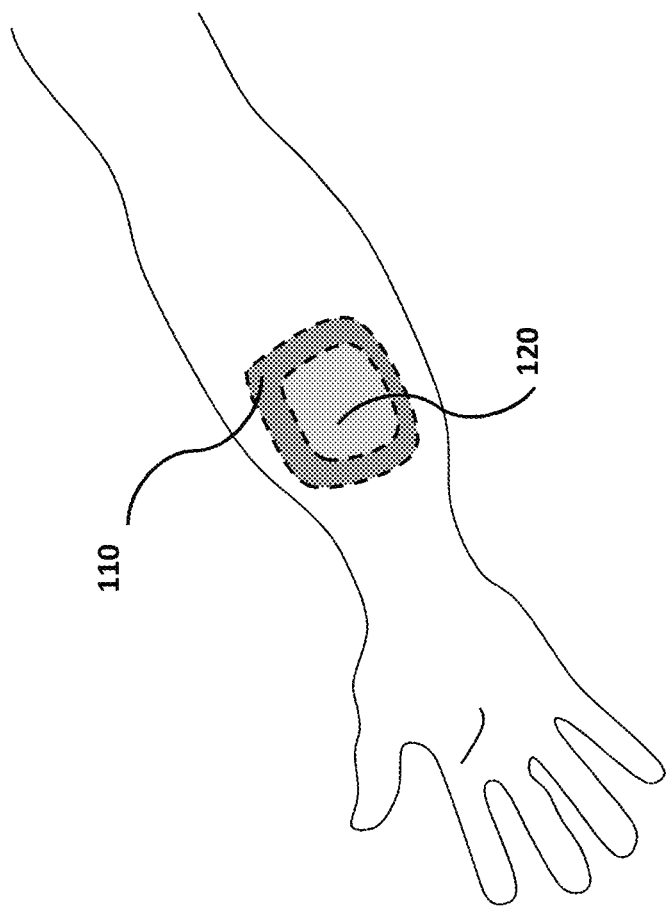
FIG. 6 is an image depicting an embodiment of the invention in which the anesthesia or analgesic is delivered through an adhesive patch. The patch can contain electrodes to transmit the electrical signal, an anesthesia reservoir containing the anesthesia, a valve system or conduits through which the anesthesia can be delivered to the patient and a feedback and control system to deliver and control the dose of the anesthesia.
Figure 7:
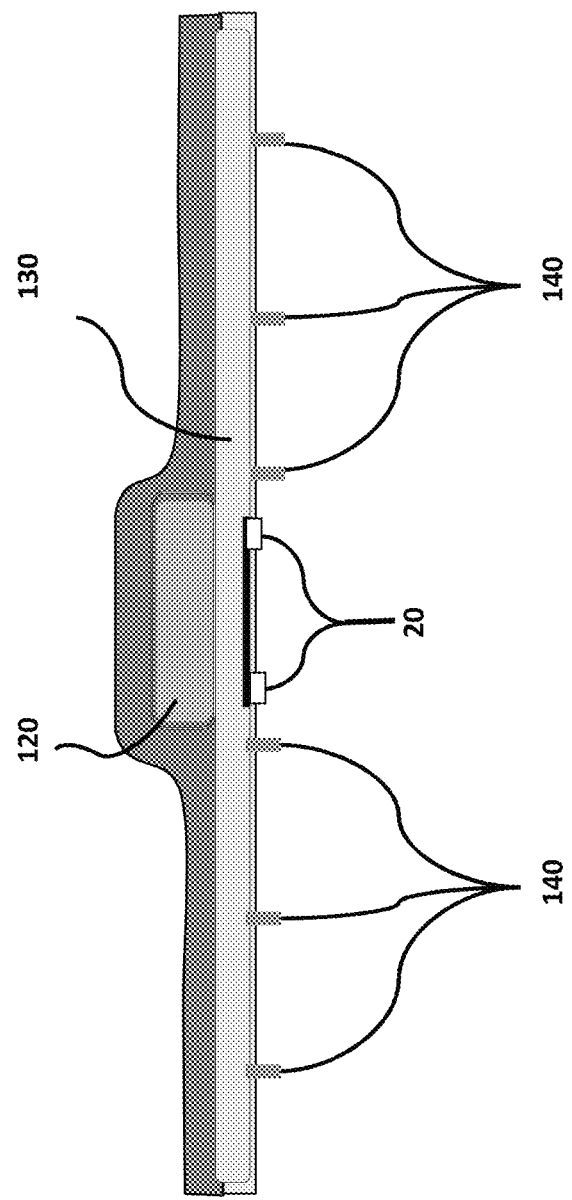
FIG. 7 is an image further depicting the patch embodiment of the present invention as described in FIG. 6. As shown in the figure, the patch contains a feedback and control unit to measure and control local anesthesia or analgesic delivery, electrodes that are in contact with tissue to measure electromagnetic or dielectric characteristics and transmit the electrical signal, an anesthetic or analgesic reservoir that contains the anesthesia to be delivered and conduits with necessary valves through which the anesthesia is delivered.

As shown in FIG. 6, an adhesive patch (110) which contains anesthesia and integrated sensing and feedback components can be attached to a patient's skin. FIG. 7 illustrates an internal view of the adhesive patch (110) of FIG. 6. The feedback and control components (120) are shown in the center of the patch (110). The patch (110) contains a hollow anesthetic or analgesic reservoir (130) that runs the length of the patch (110) and contains the anesthesia or analgesic to be administered to the patient. In one embodiment, the feedback and control components (120) are positioned above at least one electrode (20).

As shown in FIG. 7, in one possible sensing electrode configuration/arrangement there are two electrodes (20). Alternatively, there may be a single electrode (20), a plurality of electrodes (20) or an array of electrodes (20). These electrodes (20) send electrical signals to the targeted cells or tissues. Impedance or permeability of the cells or tissues to the electrical signal is transmitted back to the feedback and control components (120) which measure the electrical impedance of the cell membranes. The analysis of this impedance data in turn allows the anesthesiologist to determine the depth of anesthesia or level of sedation.

Also shown in FIG. 7 is one possible anesthetic or analgesic delivery conduit configuration/arrangement. In this configuration, there are microvalves/conduits (140) leading from the anesthetic reservoir to the patient's skin to allow the anesthesia to be delivered transdermally and control the amount of anesthesia delivered. The anesthesia can be delivered by electrical, thermal or mechanical stimulation.

Local or General Anesthesia Delivered Through Needles

Figure 8:
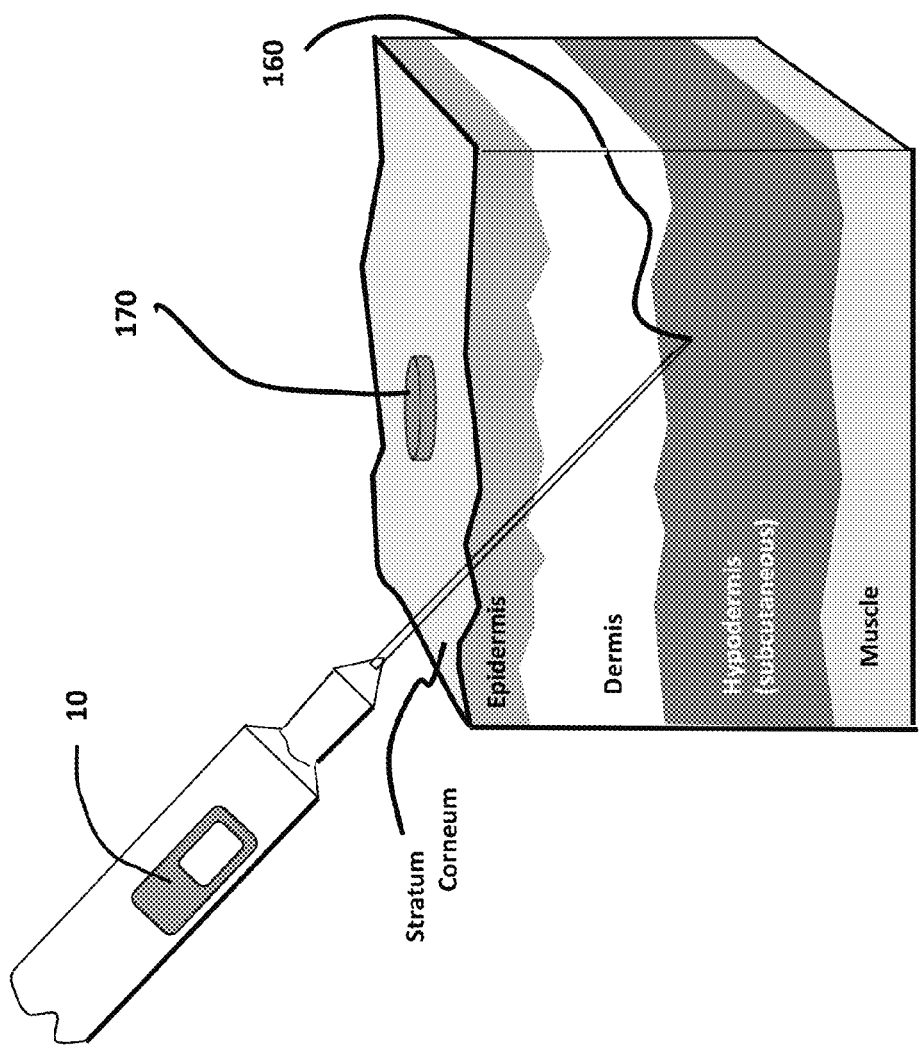
FIG. 8 is an image depicting an embodiment for a typical subcutaneous injection for the administration of local anesthesia. The syringe can contain a control unit that can be used to control the flow and dose of anesthesia. Electrodes can be located in the tip of the needle. In an alternate embodiment, the needle could be an electrode and a reference electrode could be located on the surface or at any point in the tissue or surrounding tissue.

In this embodiment, the invention can be used as a separate measurement device to assess the level of sedation and can be used with both general and local anesthesia. Alternatively, the invention can be used in conjunction with an injecting delivery system to control the amount of anesthesia or analgesic being delivered in a closed loop control mechanism. As shown in FIG. 8, the feedback and control unit (10) to assess the level of sedation can be incorporated into the base (150) of a needle (160). For local anesthesia delivery, the needle port (160) can contain a sensing electrode (20) to sense cell permeability changes within the skin. Optionally, a reference electrode (170) can be placed on the surface of the skin. This reference electrode (170) can be connected to an external control unit to control the level of sedation (not shown).

Figure 9:
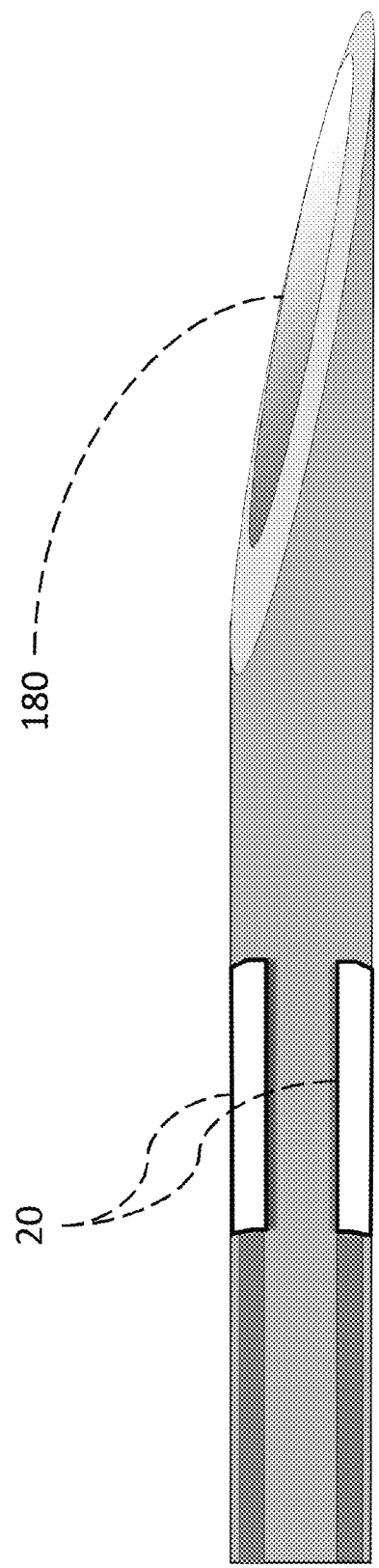
FIG. 9 is an image depicting the tip of the needle shown in FIG. 8. The needle can contain a dual electrode system for measurements and a needle orifice through which anesthesia or analgesic is delivered.

FIG. 9 is a magnified view of the embodiment shown in FIG. 8. FIG. 9 illustrates a configuration in which a pair of electrodes (20) is integrated into the needle (160) above the needle orifice (180). These electrodes (20) transmit an electrical signal to the cells/tissues. The cell permeability in response to the electrical signal is transferred back to the feedback and control unit (10) through the electrode (20). The control unit (10) measures the cell permeability by analyzing the impedance data generated from the transmission of the electrical signal. This impedance data is then correlated with the level of sedation or depth of anesthesia of the patient. There is at least one electrode (20) in the needle but in alternate embodiments, there may be a plurality or array of electrodes (20). The electrodes (20) may be wired or wireless.

Impedance spectroscopy measures the permeability of cells to electrical excitation at multiple frequencies. In the example below, two frequencies were chosen and one frequency was divided by the other to obtain a ratio. This ratio was correlated to events that the mouse was undergoing. While the example uses only two frequencies, additional frequencies can be used to yield more detailed information. As shown in FIGS. 3 and 4, both wake up events are preceded by a concave and a convex curve. An algorithm that finds local maxima and minima can be used to detect one curve or the other. One of ordinary skill in the art would recognize algorithms that could be used to analyze the data. A pseudo algorithm representing a generalized procedure is presented below as an example of an algorithm that can be used to analyze the data in a simple case. This pseudo algorithm is presented merely as a generalized example. The invention is not meant to be limited in any way to this method of analyzing the data since many other data analysis techniques can analyze the data.

Generalized Pseudo Algorithm Procedures:

Extract impedance (R(freq),X(freq)) information for all frequencies (freq)

Use Savitzky-Golay filtering algorithm to smooth R(freq) and X(freq) values for all frequencies (freq)

Calculate magnitude MAG=sqrt(R^2+Z^2)

Pick low analysis frequency range (frq1, frq2)

Pick high analysis frequency range (frq3, frq4)

Calculate average low analysis MAG values: Rlow=mean(MAG(frq1:frq2)) with mean function=sum(all values)/number of values Calculate average high analysis MAG values: Rhigh=mean(MAG(frq1:frq2)) with mean function=sum(all values)/number of values Calculate ratio MAGratio=MAGlow/MAGhigh Plot to obtain FIG. 3 in one case, plot to obtain FIG. 4 in another case Determine convex and concave portions of MAGratio(freq) to predict wake up event Example 1

Mice are C57 black mice obtained from Harlan Laboratories. Mouse 1 was put under isoflurane (at 2:50 pm) in an anesthesia chamber containing 2% Isoflurane. Mouse 1 was placed on a temperature controlled stage that was 37° C. Once Mouse 1 was asleep, a nose cone containing 5% isoflurane was introduced at 0.5 Lt/min Electrodes were placed 3.5 mm apart on the widest part of the mouse tail for the impedance spectroscopy measurements. Impedance spectroscopy measurements were made on the widest part of the mouse tail using an Aditus Cythorlab (patented method for continuous impedance measurement determines the degree of electroporation and stops the electroporation process consistently in vitro and in vivo). A reduction in breathing rate was observed 14 minutes (at 3:04 pm) after Mouse 1 was put under isoflurane in the anesthesia chamber. The isoflurane dial was changed 8 minutes later (at 3:12 pm) to 0% after reading #20. The rate of respiration increased 1 minute later at 3:13 pm. Three minutes later at 3:16 pm, Mouse 1 awakened and moved at reading #29. The data was analyzed using Matlab.

Mouse 2 was put under isoflurane (at 3:17 pm) in an anesthesia chamber containing 2.5% Isoflurane. Mouse 2 was placed on a temperature controlled stage that was 37° C. Once Mouse 2 was asleep, a nose cone containing 2.5% isoflurane was introduced at 0.5 Lt/min Electrodes were placed 3.5 mm apart on the widest part of the mouse tail for the impedance spectroscopy measurements. Impedance spectroscopy measurements were made on the widest part of the mouse tail using an Aditus Cythorlab. Measurements were started at 3:21 pm. The isoflurane dial was changed 20 minutes later (at 3:41 pm) to 0% after reading #40. The rate of respiration increased 2 minutes later at 3:43 pm. Mouse 2 awakened and moved at reading #46.

Figure 10:
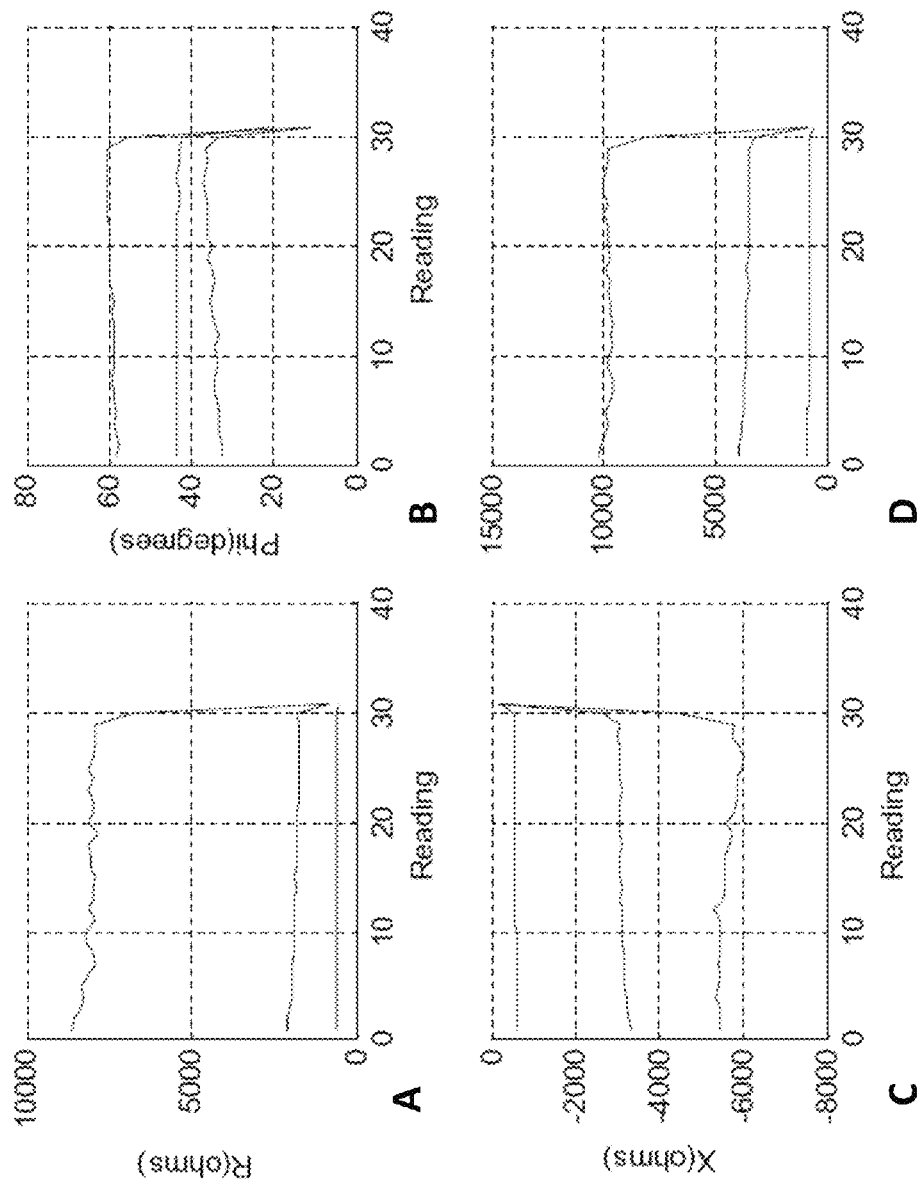
FIGS. 10A-D are a series of graphs showing (A) Resistance, (B) Reactance, (C) Phase Angle, and (D) Z Magnitude for 1 KHz, 10 KHz, and 100 KHz for mouse under 5% isoflurane.
Figure 11:
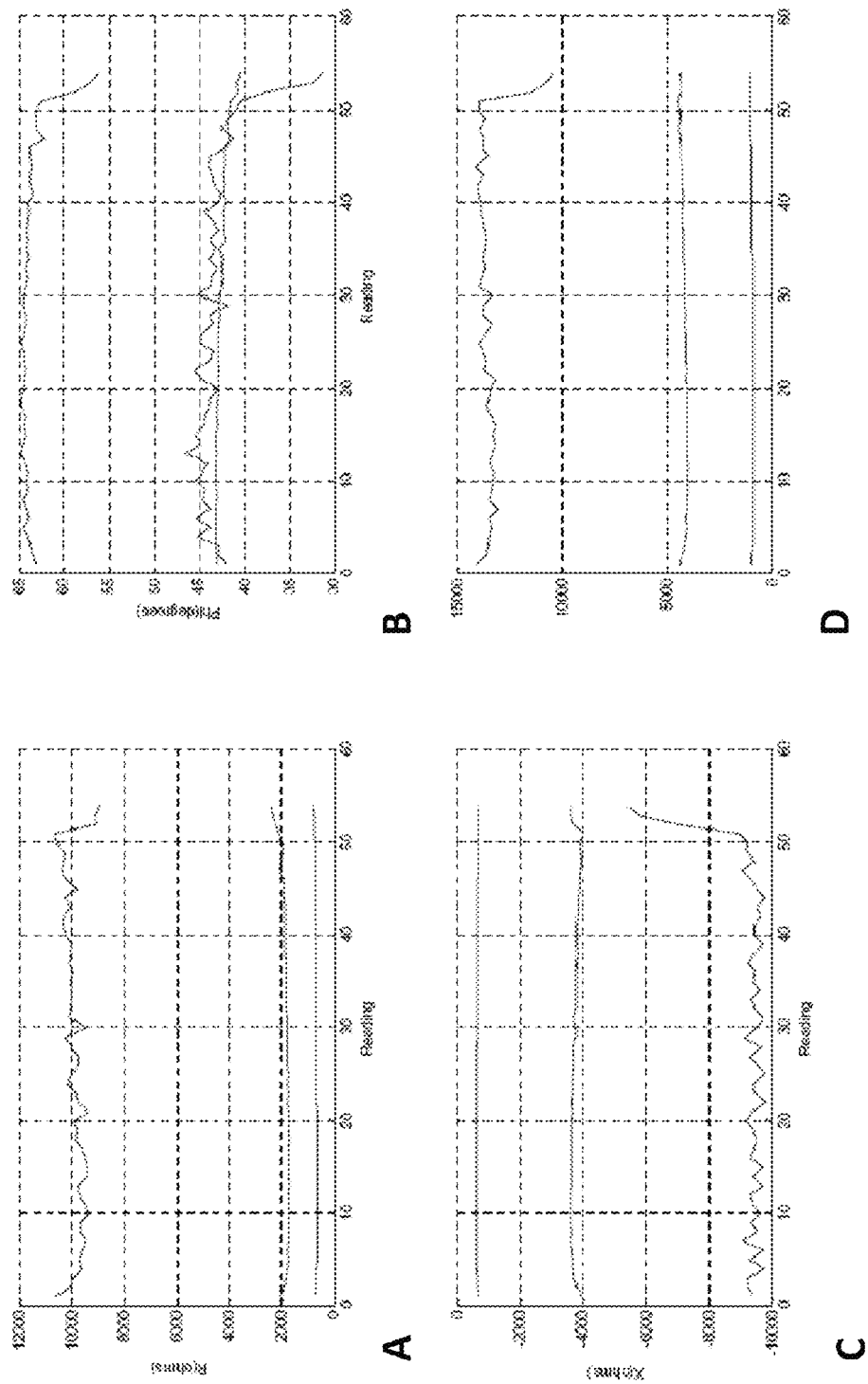
FIGS. 11A-D are a series of graphs showing (A) Resistance, (B) Reactance, (C) Phase Angle, and (D) Z Magnitude for 1 KHz, 10 KHz, and 100 KHz for mouse under 2.5% isoflurane.
Figure 12:
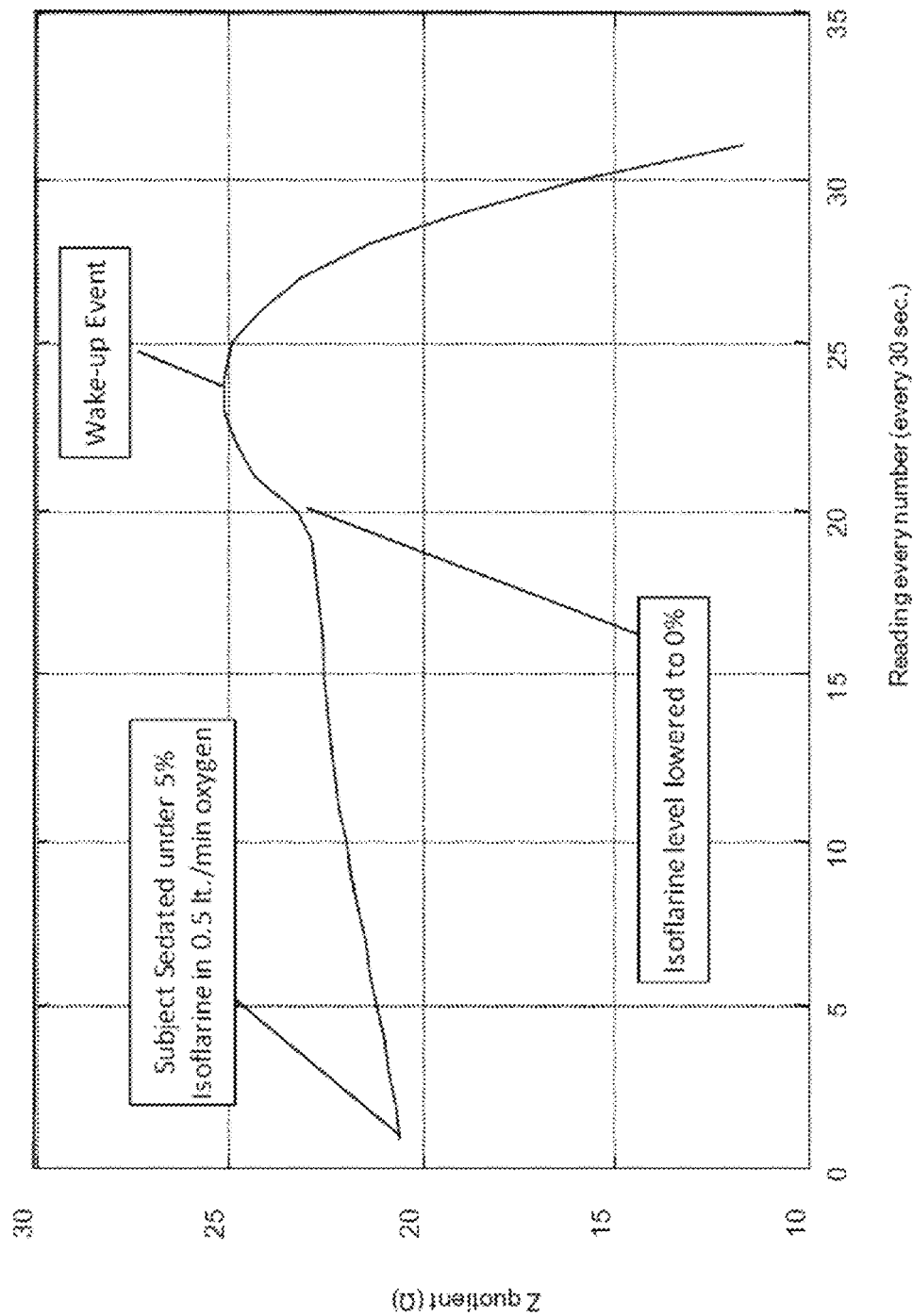
FIG. 12 is a graph depicting an impedance quotient calculated from two different frequencies which shows readings from an animal model's tissue after the subject has been sedated. During the first 20 readings the dose of isoflurane (5% isoflurante in 0.5 lt/min oxygen flow) is kept constant.

Matlab was used to extract and analyze the data from the Cythorlab text files. FIGS. 10 and 11 show impedance values for mouse 1 and 2 respectively at 1 KHz, 10 KHz, and 100 KHz. FIGS. 12 and 13 show the normalized version of the results shown in FIGS. 10 and 11. The normalization was carried out by dividing a frequency below the time constant by one above the time constant. The normalization is used to show results of tissue permeability by minimizing other effects. Cell membrane permeability of the tissue is shown in this way because a DC frequency current is easier if cells membranes are permeable. At higher frequencies the current transits through cell membranes independent of cell membrane permeability, thus the ratio of both exposes the effects of permeabilization.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of measuring depth of anesthesia in a patient comprising:
   providing at least one electrode capable of providing an electric signal to interrogate an electromagnetic property of at least one cell of the patient;
   providing a control unit which receives data from the at least one electrode wherein the control unit measures the electromagnetic property of the at least one cell; and
   correlating the measurement data to level of sedation;
   wherein the depth of anesthesia is measured using only the electromagnetic property and not a biopotential measurement.

2. The method of claim 1 wherein the electrodes are selected from the group consisting of contact electrodes, non-contact electrodes, surface electrodes, penetrating electrodes and implantable electrodes.

3. The method of claim 1 wherein the electromagnetic properties measured are selected from the group consisting of resistance, reactance, impedance, mechanical permeability, electrical permeability, capacitance, phase angle and zeta potential.

4. The method of claim 1 wherein the electromagenetic property is measured at least one frequency.

5. A method of measuring the depth of anesthesia in a patient comprising:
   providing at least one electrode to interrogate the permeability of at least one cell of the patient;
   providing a control unit which receives data from the at least one electrode wherein the control unit measures the permeability of the at least one cell to an electrical signal to generate a bioimpedance measurement; and
   correlating the measurement data to level of sedation;

wherein the depth of anesthesia is measured using only the bioimpedance measurements and no biopotential measurements.

6. The method of claim 5 wherein the electrodes are selected from the group consisting of contact electrodes, non-contact electrodes, surface electrodes, penetrating electrodes and implantable electrodes.

7. The method of claim 5 wherein the permeability of the at least one cell is measured at least one frequency.

8. A method of measuring the depth of anesthesia in a patient comprising:
   providing an electromagnetic wave propagation system to interrogate at least one electromagnetic property of at least one cell of the patient;
   providing a control unit wherein the control unit measures the at least one electromagnetic property of at least one cell of the patient; and
   correlating the measurement data to level of sedation;
   wherein the electromagnetic wave propagation system is selected from the group consisting of ion deposition waves, ultrasound waves, and microwaves.

9. The method of claim 8 wherein the electromagnetic properties measured are selected from the group consisting of resistance, reactance, impedance, mechanical permeability, electrical permeability, capacitance, phase angle and zeta potential.

10. The method of claim 8 wherein the electromagenetic property is measured at least one frequency.

11. A device for measuring the depth of anesthesia comprising:
   at least one electrode capable of providing an external electric charge to at least one cell to interrogate at least one electromagnetic property of the at least one cell;
   a control unit containing a microprocessor wherein the control unit receives data from the at least one electrode and correlates the data to the depth of anesthesia; and
   a vaporizer connected to the control unit that dispenses general anesthesia to the patient.

12. The device of claim 11 wherein the electrodes are selected from the group consisting of contact electrodes, non-contact electrodes, surface electrodes, penetrating electrodes and implantable electrodes.

13. A device for measuring the depth of anesthesia comprising an adhesive patch further comprising:
   an anesthesia reservoir disposed within the adhesive patch;
   at least one electrode disposed within the anesthesia reservoir;
   a plurality of microvalves disposed within the anesthesia reservoir; and
   a control unit containing a microprocessor wherein the control unit receives data from the at least one electrode.

14. The device of claim 13 wherein the electrodes are selected from the group consisting of contact electrodes, non-contact electrodes, surface electrodes, penetrating electrodes and implantable electrodes.

15. A device for measuring the depth of anesthesia comprising:
   a syringe further comprising:
      a hollow needle having a first and second end wherein the second end is open;
      at least one electrode disposed within the needle;
      a base fixedly connected to the first end of the needle; and
      a control unit containing a microprocessor incorporated into the base wherein the control unit receives data from the at least one electrode;
   whereby the device measures electromagnetic properties of at least one cell of a patient.

16. The device of claim 15 wherein the electrodes are selected from the group consisting of contact electrodes, non-contact electrodes, surface electrodes, penetrating electrodes and implantable electrodes.

17. The device of claim 15 wherein the electromagnetic property is selected from the group consisting of resistance, reactance, impedance, mechanical permeability, electrical permeability, capacitance, phase angle and zeta potential.

* * * * *